(12) United States Patent
Xia et al.

(10) Patent No.: US 6,703,039 B2
(45) Date of Patent: Mar. 9, 2004

(54) REVERSIBLE GELLING SYSTEM FOR OCULAR DRUG DELIVERY

(75) Inventors: Erning Xia, Penfield, NY (US); Richard V. Smerbeck, Pittsford, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 09/731,290

(22) Filed: Dec. 6, 2000

(65) Prior Publication Data

US 2002/0114778 A1 Aug. 22, 2002

(51) Int. Cl.⁷ .................................................. A61F 2/00
(52) U.S. Cl. ........................ 424/427; 424/422; 424/484; 424/486; 424/488; 424/78.17; 514/772.1
(58) Field of Search ................................ 424/422, 427, 424/78.02, 78.04, 484, 486, 488, 78.17; 514/772.4, 772.1

(56) References Cited

U.S. PATENT DOCUMENTS

| | | | |
|---|---|---|---|
| 2,703,777 A | 3/1955 | Feinstein et al. | 167/59 |
| 3,549,747 A | 12/1970 | Krezanoski et al. | 424/78 |
| 3,767,788 A | 10/1973 | Rankin | 424/78 |
| 3,767,789 A | 10/1973 | Rankin | 424/78 |
| 3,856,919 A | 12/1974 | Rankin | 424/78 |
| 3,907,985 A | 9/1975 | Rankin | 424/78 |
| 3,947,573 A | 3/1976 | Rankin | 424/80 |
| 3,987,163 A | 10/1976 | Rankin | 424/78 |
| 4,029,817 A | 6/1977 | Blanco et al. | 424/329 |
| 4,120,949 A | 10/1978 | Bupatla et al. | 424/80 |
| 4,131,651 A | 12/1978 | Shah et al. | 424/78 |
| 4,409,205 A | 10/1983 | Shively | 424/78 |
| 4,525,346 A | 6/1985 | Stark | 424/80 |
| 4,888,168 A | 12/1989 | Potts et al. | 424/78 |
| 5,106,615 A | 4/1992 | Dikstein | 424/78.04 |
| 5,141,665 A | 8/1992 | Sherman | 252/106 |
| 5,405,878 A | * 4/1995 | Ellis et al. | 422/28 |
| 5,457,093 A | 10/1995 | Cini et al. | 514/12 |
| 5,591,426 A | 1/1997 | Dabrowski et al. | 424/78.04 |
| 5,705,485 A | * 1/1998 | Cini et al. | 514/12 |

FOREIGN PATENT DOCUMENTS

WO    WO 96 20696    7/1996    ............ A61K/9/14

* cited by examiner

*Primary Examiner*—Thurman K. Page
*Assistant Examiner*—Liliana Di Nola-Baron
(74) *Attorney, Agent, or Firm*—Rita D. Vacca; Denis A. Polyn; Robert D. Furr, Jr.

(57) ABSTRACT

The invention provides an ophthalmic aqueous composition for topical administration, comprising:

(a) a block copolymer of propylene oxide and ethylene oxide in concentration sufficient to provide viscosity of less than about 25 centipoise at ambient temperature and viscosity of from about 25 to about 55 centipoise when applied topically to a patient;

(b) hydroxypropyl methylcellulose in concentration sufficient to improve the durability of the gel formed by the block copolymer.

The invention further provides a method for administering ophthalmic pharmaceuticals.

18 Claims, 1 Drawing Sheet

REVERSIBLE GELLING SYSTEM FOR OCULAR DRUG DELIVERY

FIELD OF THE INVENTION

The present invention is directed to ophthalmic compositions, particularly those provided as buffered, aqueous solutions. The subject compositions are useful as moisturizing and lubricating eye drops and as delivery vehicles for ophthalmic drugs.

BACKGROUND

Ophthalmic compositions used for the treatment of "dry eye" symptoms include demulcents (or humectants) for lubricating mucous membrane surfaces and for relieving dryness and irritation. The term "demulcent", as used herein is intended to mean an agent, usually a water-soluble polymer, which is applied topically to the eye to protect and lubricate mucous membrane surfaces and relieve dryness and irritation. Within this meaning, the terms "humectant" and "wetting agent" are also commonly used. Furthermore, it will be understood that some constituents possess several functional attributes. For example, cellulose derivatives are common demulcents, but are also used as "viscosity increasing agents". Similarly, glycerin is a known demulcent but is also used as a "tonicity adjusting agent". Examples of the most widely used demulcents include: polyvinyl alcohol, polyvinyl pyrrolidone, cellulose derivatives and polyethylene glycol.

Specific examples of known ophthalmic compositions including various demulcents are provided below.

U.S. Pat. No. 5,591,426 to Dabrowski et al. discloses an ophthalmic solution useful as an artificial tear. The reference includes a specific example of a borate buffered, preserved (e.g. benzalkonium chloride), aqueous solution including the following three demulcents: 1) glycerin, 2) polyvinyl pyrrolidone, and 3) a cellulose derivative, e.g. hydroxypropyl methyl cellulose.

U.S. Pat. No. 5,106,615 to Dikstein discloses isotonic humectant eyedrops including glycerin, polyethylene glycol, or propylene glycol with an anionic polymer such as Carbomer 941.

U.S. Pat. No. 2,703,777 to Feinstein et al. generally describes a preserved, buffered, isotonic ophthalmic gel including: 1) a humectant, preferably glycerin (sorbitol and propylene glycol are also listed); 2) methyl cellulose, and 3) polyethylene glycol.

U.S. Pat. No. 4,029,817 to Blanco et al. discloses a contact lens preserving solution including propylene glycol in combination with polysorbate 80 and/or polyvinyl pyrrolidone. Similarly, U.S. Pat. No. 5,141,665 to Sherman discloses a contact lens cleaning, wetting and storing solution which includes propylene glycol as a wetting agent. Also, U.S. Pat. No. 4,525,346 to Stark discloses a borate buffered, preserved contact lens solution including propylene glycol.

U.S. Pat. Nos. 3,767,788; 3,767,789; 3,856,919; 3,907,985; 3,920,810; 3,947,573; 3,987,163 all to Rankin disclose ophthalmic solutions for the treatment of "dye eye". These references generally teach the use of polyethylene oxide, polystyrene sulfonate, and polyacrylamide, with polyalkylene glycols, e.g. polyethylene glycol or propylene glycol. These references include specific example solutions including several demulcents combined with one another; namely, 1) polyethylene glycol, 2) polyvinyl pyrrolidone and a 3) cellulose derivative, e.g. hydroxy ethyl cellulose.

U.S. Pat. No. 3,549,747 to Krezanoski et al. discloses a preserved contact lens wetting solution including polyvinyl alcohol with a cellulose derivative, e.g. hydroxy ethyl cellulose. Similarly, U.S. Pat. No. 4,131,651 to Shah et al. discloses an ophthalmic solution for the treatment of dry eye which includes polyvinyl alcohol with a cellulose derivative. U.S. Pat. No. 4,120,949 to Bapatla et al. discloses a preserved ophthalmic solution including 1) polyvinyl alcohol, 2) polyvinylpyrrolidone, and 3) one or more cellulose derivatives. Also similarly, U.S. Pat. No. 4,409,205 to Shively discloses a specific example of a preserved ophthalmic solution including: polyvinyl alcohol, polyethylene glycol 6000, and dextrose. This reference also generally discloses the use of tonicity adjusting agents selected from the group of: mannitol, sorbitol, dextrose, sucrose, urea, and glycerin.

Techniques for formulating gels for delivering ophthalmically active drugs topically are known in the art, see for example GB-A-No. 2013084 disclosing aqueous pre-formed pharmaceutical gels for application to the conjunctival sac of the eye, and GB-A-No. 1571832 and EP-A-No. 0126684 disclosing drug delivery systems in the form of liquids which gel in situ when warmed by the body of the patient and useful in the treatment of a variety of ocular conditions. Similarly, U.S. Pat. No. 4,888,168 to Potts et al. and U.S. Pat. No. 5,800,807 to Hu et al. disclose a gel systems for delivering ophthalmic drugs.

The goal of designing an ophthalmic gel is to make the gel sufficiently flowable that the gel can be conveniently applied to the eye, while at the same time providing a gel that is viscous enough to prolong residence time (contact time) in the eye. But the viscosity at body temperature of known in situ gelling systems can be difficult to predict with certainty. Gels having viscosities above about 55 centipoise (cps) can be uncomfortable and aesthetically unattractive in the eye. For this reason, it is critical to provide an ophthalmic gel that provides the desired residence time while avoiding the discomfort and unattractive cosmetic appearance of a substantially solidified gel.

Thus it would be desirable to provide an ophthalmic gel that improves the contact time between the target ocular tissue and an active pharmaceutical agent, while also overcoming the problems associated with high viscosity gels. It would also be desirable to improve the durability and the useful life of the gel composition once formed to further prolong contact time with the target ocular tissue.

SUMMARY OF THE INVENTION

The present invention provides an ophthalmic gel composition that effectively prolongs residence time in the eye while at the same time being more comfortable and easier to apply. This invention relates to the treatment of eye conditions using pharmaceutical preparations that gel in situ when applied to the patient. Suitable active pharmaceutical agents include beta blockers, carbonic anhydrase inhibitors, ophthalmic decongestants, antihistamines, antibiotics and antiinflamatories, merely to name a few.

In one embodiment, the subject composition is provided as a buffered, aqueous solution which includes a demulcent, preferably a cellulose derivative. The subject composition may be unpreserved (provided in a single dose format), or may be preserved, e.g. with benzylalkonium chloride, PHMB, sorbic acid, etc.

The invention provides, in one embodiment, an ophthalmic aqueous composition for topical administration, comprising:

(a) a block copolymer of propylene oxide and ethylene oxide in concentration sufficient to provide viscosity of less than about 25 centipoise at ambient temperature and viscosity of from about 25 to about 55 centipoise when applied topically to a patient; and (b) hydroxypropyl methylcellulose in concentration sufficient to improve the durability of a gel formed by the block copolymer.

The block copolymer of propylene oxide and ethylene oxide preferably comprises at least one propylene oxide block sandwiched between two ethylene oxide blocks. This is commonly referred to as an ABA block copolymer. In a particularly preferred embodiment, the composition of the block has the chemical formula:

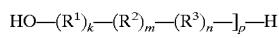

where
$R^1$ is —CH$_2$CH$_2$O—;
$R^2$ is —CH$_3$CH CH$_2$O—;
$R^3$ is —CH$_2$CH$_2$O—;
k is from 2 to 128;
m is from 16 to 67; and
p is from 2 to 128.

The most preferred block copolymeric surfactants include:

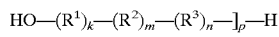

where
$R^1$ is —CH$_2$CH$_2$O—;
$R^2$ is —CH$_3$CH CH$_2$O—;
$R^3$ is —CH$_2$CH$_2$O—;
k is about 98 (average);
m is about 67 (average); and
p is about 98 (average).

The methylcellulose useful in the present invention is preferably hydroxpropyl methylcellulose. The preferred hydroxypropyl methylcellulose composition preferred for use in the present invention has the chemical formula shown below. One particularly preferred group of methylcellulose compositions is sold under the tradename "Methocel" by the Dow Chemical Company of Midland, Mich. Examples of useful methylcellulose compositions include Methocel A, E, F, J and K, as well as the Methocel 310 series of compositions. For the composition of the present invention, Methocel E is the most preferred Methocel brand composition.

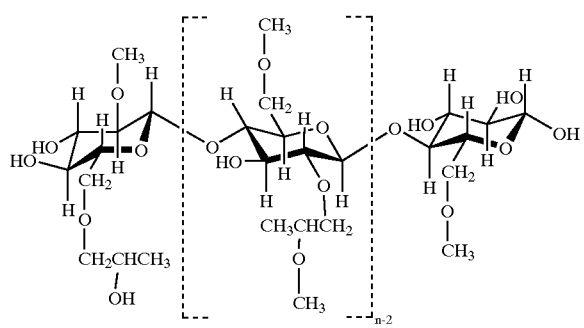

The most preferred METHOCEL is METHOCEL E.

The invention provides, in another embodiment, a method for administering an ophthalmic drug comprising topically applying a sterile ophthalmic solution to a patient's eye, said solution comprising (a) a block copolymer of propylene oxide and ethylene oxide in concentration sufficient to provide viscosity of less than about 25 centipoise at ambient temperature and viscosity of from about 25 to about 55 centipoise when applied topically to a patient; and (b) hydroxypropyl methylcellulose in concentration sufficient to improve the durability of the gel formed by the block copolymer.

DETAILED DESCRIPTION OF THE INVENTION

Figure 1:
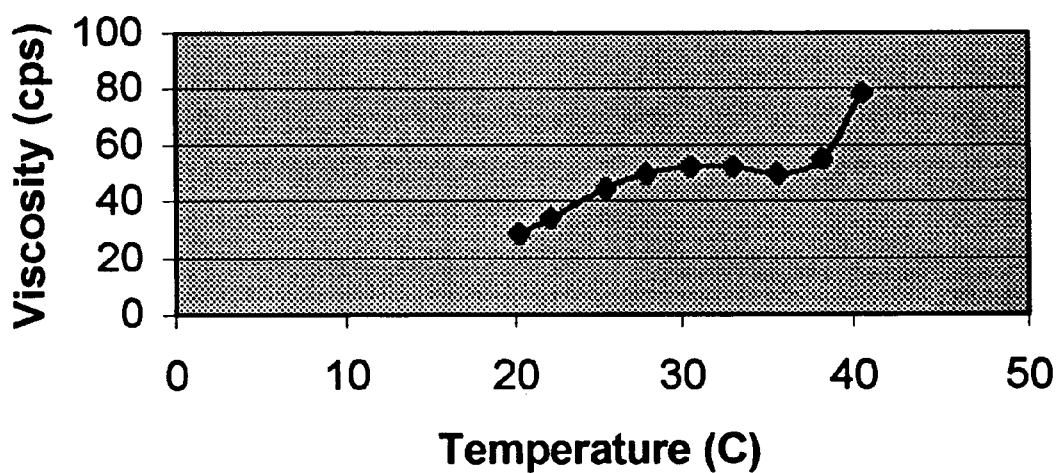
FIG. 1 is a chart profiling viscosity versus temperature for the solution of Example 1.

As previously described, the subject composition finds particular utility as a moisturizing and lubricating eye drop (i.e. an artificial tear solution), a delivery vehicle for ophthalmic drugs, and as a contact lens wetting and lubricating solution. In most of these applications, the subject composition is provided as a buffered aqueous solution. Such a solution typically has a viscosity (at ambient temperatures) of from about 1 to about 25 centipoise (cps).

The present ophthalmic compositions include hydroxypropyl methylcellulose and a block copolymer surfactant, for example, a block copolymer of propylene oxide and ethylene oxide in which the propylene oxide block is sandwiched between two ethylene oxide blocks.

Suitable block copolymer surfactants include those surfactants having the formula:

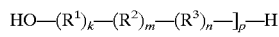

where
$R^1$ is —CH$_2$CH$_2$O—;
$R^2$ is —CH$_3$CH CH$_2$O—;
$R^3$ is —CH$_2$CH$_2$O—;
k is from 2 to 128;
m is from 16 to 67; and
p is from 2 to 128.

Preferred examples of such block copolymers include the PluronicTm brand surfactants commercially available from BASF Corporation.

The cellulose derivatives useful in the invention include: hydroxypropyl methylcellulose, carboxymethyl cellulose, methyl cellulose, hydroxyethyl cellulose, merely to name a few. In a preferred embodiment, the composition comprises hydroxypropyl methylcellulose. Suitable concentration ranges are shown below.

TABLE 1

Solution Composition

| | Useful concentration range (weight percent) | Preferred concentration range (weight percent) | More preferred concentration range (weight percent) |
|---|---|---|---|
| Hydroxymethyl propylcellulose | 0.1 to 2.0 | 0.2 to 1.0 | 0.4 to 0.8 |
| Block copolymer surfactant | 5 to 25 | 7 to 18 | 10 to 15 |

Other demulcents may be included in the composition, to the extent that they are compatible with effecting the desired increase in viscosity with temperature. Examples of suitable demulcents may include polyvinyl pyrrolidone, polyvinyl alcohol, polyethylene glycol, and other components such as polyethylene oxide, and polyacrylic acid are specifically excluded. In still other embodiments, other or additional demulcents may be used in combination with glycerin and propylene glycol. For example, polyvinyl pyrrolidone, polyvinyl alcohol, may also be used.

The demulcents used in the present invention are used in effective amounts (i.e. "demulcifing amounts") for providing a demulcifing effect, i.e. sufficient to lubricating mucous membrane surfaces and to relieve dryness and irritation. The specific quantities of demulcents used in the present invention will vary depending upon the application; however, typically ranges of several demulcents are provided: glycerin: from about 0.2 to about 1.5%, but preferably about 1% (w/w); propylene glycol: from about 0.2 to about 1.5%, but preferably about 1% (w/w); cellulose derivative: from about 0.2 to about 3%, but preferably about 0.5% (w/w). If additional demulcents are used, they are typically used in quantities specified in the over-the-counter monograph, cited above. A preferred cellulose derivative is pharmaceutical grade hydroxypropyl methylcellulose (HPMC), such as Methocel E 15 LV-premium, available from Dow Chemical Company.

When used, any pharmaceutically acceptable buffer system may be utilized; however, a preferred buffer system is provided by sodium phosphate (both dibasic and monobasic) in amounts necessary to produce a pH of about 6.0 to about 8.0, but more preferably from about 7.0 to about 7.6.

The composition may be designed for a variety of osmolalities, but in most applications, iso-osmolal (with respect to the fluids of the eye) compositions are preferred. Osmolalities typically range from about 175 to about 330 mOsm/kg, but more preferably from about 280 to about 320 mOsm/kg. The osmolality of the solution may be adjusted by means of well known osmolality adjusting agents, e.g. sodium chloride and potassium chloride, and organic osmolytes.

As previously indicated, the subject composition may include a preservative in an amount effective to preserve the solution. As is known in the art, the amount of preservative required will vary upon the specific preservative and the application, e.g. moisturizing eye drop, contact lens solution, etc. For non-contact lens applications, benzalkonium chloride (BAK) is a preferred preservative typically used in concentrations from about 0.01 to about 0.10%(w/w). BAK is a well known preservative which comprises a mixture of alkyldimethyl benzylammonium chlorides. For contact lens applications, other preservatives are more preferred, such as sorbic acid, PHMB, and other polyquats. Alternatively, the subject compositions may be preservative-free.

The composition may include a number of additional components. For example, the solution may include edetate disodium as a co-preservative and/or chelating agent.

EXAMPLE I

As an illustration of the present invention, a preferred moisturizing eye drop formulation is provided below.

TABLE 2

| Ingredients | % w/w |
|---|---|
| Pluronic F-127 | 12.50 |
| Hydroxypropyl Methylcellulose (HPMC) | 0.50 |
| Sodium Phosphate (Dibasic) | 0.19 |
| Sodium Phosphate (Monobasic) | 0.052 |
| Sodium Chloride (NaCl) | 0.84 |
| Edetate Disodium (EDTA) | 0.10 |
| Benzalkonium Chloride (BAK) (50%) | 0.02 |
| Purified Water | q.s. to 100% |

The solution was prepared by dissolving the HPMC in hot purified water (85% of total weight of batch) and mixed for 20 minutes. The HPMC solution was cooled to 5° C. and mixed again for 30 minutes. Pluronic F127 and other raw materials were then added into the batch and mixed for more than two hours.

EXAMPLE II

The viscosity profile of the solution from Example 1 as a function of temperature was determined by Brookfield Viscometer (see FIG. 1.). The solution from Example 1 is liquid at room temperature, and at higher temperature (eye temperature).

EXAMPLE III

An antihistamine drug was added to phosphate buffer alone and the complete solution from Example 1, respectively. New Zealand white rabbits, free from visible ocular defects, each received a single intraocular application of 30 microliters of test article in one eye. The contralataral eye, treated with 100 microliters of control article served as a control. The animals were then divided into four groups. The animals in the first group received a single intraocular application of 100 microliters of test article (Histamine solution) in both eyes one hour after the initial treatment. The animals in the second group received this identical treatment two hours after treatment and those in the third group, four hours after the initial treatment and those in the fourth group, six hours after the initial treatment. The eyes of all animals remained unwashed. Observations of corneal opacity, iritis, and conjunctivitis were recorded ten minutes after the test article (Histamine solution) treatment. The results from rabbit tests showed that there is a significant change of duration time of action in terms of reducing redness induced by histamine solution between test group and control group. Block copolymer gels are formed at body temperature by hydrogen bonding in aqueous system, caused by the attraction of the surfactant ether oxygen atoms with hydrogen protons.

TABLE 3

Comparison of Duration Time of Action Between Test Group and Control Group.

|  | Test Group | Control Group (Phosphate Buffer) |
| --- | --- | --- |
| Duration Time (Hours) | 6–8 Hours | 0–1 Hours |

EXAMPLE IV

An antihistamine drug was added into the complete solution from Example 1 with and without HPMC, respectively. The results from rabbit tests showed that there is a significant change of duration time of action in terms of reducing redness induced by histamine solution between both test groups. Addition of HPMC (METHOCEL E) can strengthen block copolymer gel. Inorganic salts or strong electrolytes soften gels. Any material added to a gel system may affect the gel's strength and achieve the desired product properties.

TABLE 4

Comparison of Duration Time of Action Between Both Test Groups

|  | Test Group (With HPMC) | Test Group (Without HPMC) |
| --- | --- | --- |
| Duration Time (Hours) | 6–8 Hours | 4–6 Hours |

We claim:

1. An ophthalmic aqueous composition for topical administration suitable as a delivery vehicle for ophthalmic drugs, comprising:
   (a) a block copolymer of propylene oxide and ethylene oxide in concentration sufficient to provide viscosity of less than about 25 centipoise at ambient temperature and viscosity of from about 25 to about 55 centipoise when applied topically to a patient; and
   (b) hydroxypropyl methylcellulose in concentration sufficient to improve the durability of the gel formed by the block copolymer.

2. The ophthalmic aqueous composition of claim 1 further comprising a germicidial agent in a sufficient amount of preserve sterility of the composition.

3. The composition of claim 1 wherein said block copolymer of propylene oxide and ethylene oxide further comprises at least one propylene oxide block sandwiched between two ethylene oxide blocks.

4. The composition of claim 3 wherein said block copolymer has the chemical formula:

$$\text{HO}—(R^1)_k—(R^2)_m—(R^3)_n—]_p—H$$

where
   $R^1$ is —$CH_2CH_2O$—;
   $R^2$ is —$CH_3CHCH_2O$—;
   $R^3$ is —$CH_2CH_2O$—;
   k is from 2 to 128;
   m is from 16 to 67; and
   p is from 2 to 128.

5. The composition of claim 4 further comprising from about 5 to about 25 weight percent block copolymer and from about 0.1 to about 2.0 weight percent hydroxypropyl methylcellulose.

6. The composition of claim 5 further comprising from about 7 to about 18 weight percent block copolymer and from about 0.2 to about 1.0 weight percent hydroxypropyl methylcellulose.

7. The composition of claim 6 further comprising from about 10 to about 15 weight percent block copolymer and from about 0.4 to about 0.8 weight percent hydroxypropyl methylcellulose.

8. The composition of claim 4 further comprising a buffering agent.

9. The composition of claim 8, including a buffering agent selected from the group consisting of boric acid/sodium borate, dibasic sodium phosphate and monobasic sodium phosphate.

10. A method for administering an ophthalmic drug comprising topically applying a sterile ophthalmic solution to a patient's eye, said solution comprising:
   (a) a block copolymer of propylene oxide and ethylene oxide in concentration sufficient to provide viscosity of less than about 25 centipoise at ambient temperature and viscosity of from about 25 to about 55 centipoise when applied topically to a patient; and
   (b) hydroxypropyl methylcellulose in concentration sufficient to improve the durability of the gel formed by the block copolymer.

11. The method of claim 10 wherein the ophthalmic solution further comprises a germicidial agent in a sufficient amount of preserve sterility of the composition.

12. The method of claim 10 wherein said block copolymer of propylene oxide and ethylene oxide further comprises at least one propylene oxide block sandwiched between two ethylene oxide blocks.

13. The composition of claim 12 wherein said block copolymer has the chemical formula:

$$\text{HO}—(R^1)_k—(R^2)_m—(R^3)_n—]_p—H$$

where
   $R^1$ is —$CH_2CH_2O$—;
   $R^2$ is —$CH_3CHCH_2O$—;
   $R^3$ is —$CH_2CH_2O$—;
   k is from 2 to 128;
   m is from 16 to 67; and
   p is from 2 to 128.

14. The method of claim 13 wherein the ophthalmic composition further comprises from about 5 to about 25 weight percent block copolymer and from about 0.1 to about 2.0 weight percent hydroxypropyl methylcellulose.

15. The method of claim 14 wherein the ophthalmic composition further comprises from about 7 to about 18 weight percent block copolymer and from about 0.2 to about 1.0 weight percent hydroxypropyl methylcellulose.

16. The method of claim 15 wherein the ophthalmic composition further comprises from about 10 to about 15 weight percent block copolymer and from about 0.4 to about 0.8 weight percent hydroxypropyl methylcellulose.

17. The method of claim 14 wherein the ophthalmic composition further comprises a buffering agent.

18. The method of claim 17 wherein the buffering agent is selected from the group consisting of boric acid/sodium borate, dibasic sodium phosphate and monobasic sodium phosphate.

* * * * *